US006118036A

United States Patent [19]

Zinnen

[11] Patent Number: 6,118,036

[45] Date of Patent: Sep. 12, 2000

[54] ALKANE ISOMERIZATION USING REVERSIBLE FLOW

[75] Inventor: Herman A. Zinnen, Evanston, Ill.

[73] Assignee: UOP LLC, Des Plaines, Ill.

[21] Appl. No.: 09/247,180

[22] Filed: Sep. 24, 1998

[51] Int. Cl.[7] ...................................................... C07C 5/13

[52] U.S. Cl. ......................... 585/738; 585/734; 585/739; 585/744; 585/750; 585/751

[58] Field of Search .................................... 585/734, 738, 585/739, 744, 750, 751

[56] References Cited

U.S. PATENT DOCUMENTS

| | | | |
|---|---|---|---|
| 4,783,574 | 11/1988 | Barnes | 585/738 |
| 5,744,684 | 4/1998 | Zinnen et al. | 585/737 |

*Primary Examiner*—Walter D. Griffin
*Assistant Examiner*—Tam M. Nguyen
*Attorney, Agent, or Firm*—John G. Tolomei; Frank S. Molinaro; Maryann Maas

[57] ABSTRACT

A process to isomerize at least one normal or mono-methyl-branched alkane to form at least one multi-methyl-branched alkane has been developed. At least one normal or mono-methyl-branched is introduced to a reaction zone to form at least one multi-methyl-branched alkane. The reaction zone is located between a first and a second adsorption zone with the adsorption zones containing an adsorbent effective to selectively adsorb normal and mono-methyl-branched alkanes relative to multi-methyl-branched alkanes. A desorbent is introduced to the first adsorption zone and an effluent containing at least one multi-methyl-branched alkane is withdrawn from the second adsorption zone. After a period of time, the introduction of the desorbent is redirected to the second adsorption zone and concurrently the withdrawal of the effluent is moved to the first adsorption zone.

11 Claims, No Drawings

ALKANE ISOMERIZATION USING REVERSIBLE FLOW

FIELD OF THE INVENTION

The invention relates to the isomerization of an alkane having from about 6 to about 8 carbon atoms in a reaction zone that is located between two adsorption zones. The fluid flow in the adsorption zone reaction zone adsorption zone system is periodically reversed to retain the reactants within the system until the reactants are converted to isomerized products.

BACKGROUND OF THE INVENTION

Alkane isomerization processes are widely used by refiners to convert normal and mono-methyl-branched $C_6$ alkanes into more valuable branched alkanes. The multi-methyl-branched $C_8$ alkanes have a higher octane number and are used as gasoline blending components to boost the octane number of the gasoline. Normal and mono-methyl-branched $C_7$ alkanes have been converted into benzene and other valuable aromatic hydrocarbons for gasoline blending by catalytic reforming. However, due to environmental concerns, the demand for aromatics in the future may diminish. The present invention, an alkane isomerization process using reversible flow, is an alternate refining process for the normal and mono-methyl-branched $C_7$ and $C_8$ alkanes that yields a high octane number product. The isomerized $C_7$and $C_8$ products may be used as octane number boosters in gasoline blending instead of benzene and other aromatics.

Typically, commercial isomerization processes have had at least a two-stage design; the first stage is a fixed bed reactor and the second stage is a separation unit; see for example U.S. Pat. No. 5,146,037 and U.S. Pat. No. 5,245,102. The isomerization that takes place in the fixed bed reactor is limited by thermodynamic equilibrium which results in the reactor effluent containing a substantial amount of unconverted alkanes. The separation unit, which is usually either an adsorption or a fractionation unit, is used to separate the unconverted alkanes from the isomerized product alkanes. The adsorption unit may be one or more beds of different adsorbent each performing a different separation as in U.S. Pat. No. 5,059,741, U.S. Pat. No. 4,855,529 and U.S. Pat. No. 4,804,802. The unconverted alkanes are generally recycled to the fixed bed reactor. With this type of design, the recycle stream is usually substantial, and methods of increasing the yield of highly branched alkanes are in demand.

U.S. Pat. No. 4,783,574 describes reversing an inert hydrogen sweep flow over separate zones of catalyst and adsorbent. A fixed bed reactor contained a sub-bed of adsorbent at each end and one sub-bed of catalyst in the center. The feed was introduced near the catalyst sub-bed, and a hydrogen sweep fluid was introduced at one end of the reactor. The isomerization was catalyzed and unconverted normal alkane reactants were adsorbed on the adsorbent sub-bed downstream of the catalyst sub-bed in the direction of the hydrogen flow. Branched alkanes were not adsorbed and were removed from the reactor. Then the inert sweep fluid flow was reversed by introducing the hydrogen from the opposite end of the reactor to sweep the unconsumed normal alkane reactants back to the catalyst sub-bed.

The present invention makes use of reversible flow to perform isomerization of hydrocarbons containing from about 6 to about 8 carbon atoms. The above reversible flow operations are designed to reduce normal alkane content without specificity as to desired branched products. The above reversible flow fixed bed references do not teach separating multi-methyl-branched alkanes from normal and mono-methyl-branched alkanes in order to optimize the process for specifically multi-methyl branched alkane production. The above reversible flow fixed bed references also fail to teach alkane desorbents that are effective for separation and further fail to teach reactive alkane desorbents. The present invention uses reversible flow to isomerize alkanes having from about 6 to about 8 carbon atoms and to separate product multi-methyl-branched alkanes from normal and mono-methyl-branched alkanes. Furthermore, in the present invention the desorbent is an alkane, thus eliminating the need for regeneration of the adsorbent as required in the previous references that use hydrogen to purge unreacted alkanes from the adsorbent.

Reactive chromatography has also been used for isomerization of alkanes; see U.S. Pat. No. 3,122,494, U.S. Pat. No. 5,530,172, U.S. Pat. No. 5,530,173, U.S. Pat. No. 5,763,730, U.S. Pat. No. 5,744,684, U.S. Pat. No. 5,744,683, and U.S. Pat. No. 5,770,783. However, the present invention does not make use of reactive chromatography.

SUMMARY OF THE INVENTION

The purpose of the invention is to isomerize at least one normal or mono-methyl-branched alkane containing from about 6 to about 8 carbon atoms to form at least one multi-methyl-branched alkane. The process begins by introducing at least one normal or mono-methyl-branched alkane containing from about 6 to about 8 carbon atoms to a reaction zone to isomerize the normal or mono-methyl-branched alkane and form at least one multi-methyl-branched alkane. The reaction zone (I) is operated under conditions effective for the isomerization, (II) contains a catalyst effective to catalyze the isomerization, (III) has a hydrogen atmosphere so that the mole ratio of hydrogen to hydrocarbon in the reaction zone is in the range of about 0.1 to about 2, and (IV) is located between a first and a second adsorption zone. The first and second adsorption zones contain an adsorbent effective to selectively adsorb normal and mono-methyl-branched alkanes relative to multi-methyl-branched alkanes. A desorbent having at least one alkane having from about 4 to about 8 carbon atoms is introduced to the first adsorption zone and an effluent containing at least one multi-methyl-branched alkane is withdrawn from the second adsorption zone. After a period of time, the introduction of the desorbent is redirected to the second adsorption zone and concurrently the location of the withdrawal of the effluent is moved to the first adsorption zone. The periodic alternate introduction of the desorbent to the first adsorption zone and then the second adsorption zone with concurrent alternation of the withdrawal of the effluent from the second adsorption zone and then the first adsorption zone is continued.

DETAILED DESCRIPTION OF THE INVENTION

This invention is a process for isomerizing an alkane to produce valuable multi-methyl-branched alkanes using reversible flow. In general terms, the invention is carried out by introducing a reactant alkane to a reaction zone containing a catalyst effective for isomerization. The reaction zone is located between two adsorption zones each containing an adsorbent capable of adsorbing normal and mono-methyl-branched alkanes relative to multi-methyl-branched alkanes. For catalyst stability, the reaction zone is maintained in a hydrogen atmosphere. A desorbent containing an alkane having from about 4 to about 8 carbon atoms is introduced to the first adsorption zone. The reactant alkane is isomerized with the aid of the catalyst and the isomerized products may consist of mono-methyl-branched alkanes and multi-methyl-branched alkanes. The reaction mixture moves with the fluid flow and is carried from the reaction zone to the second adsorption zone. In the second adsorption zone the desired multi-methyl-branched alkanes are separated from any unreacted normal alkane reactant or mono-methyl-branched alkane that are adsorbed by the adsorbent. The multi-methyl-branched alkane product will be least adsorbed by the adsorbent relative to the normal and mono-methyl-branched alkanes and thus will be carried unhindered with the flow of the desorbent and removed from the zone. The normal and mono-methyl-branched alkanes will gradually fill the capacity of the adsorbent and will eventually reach the point where additional normal or mono-methyl-branched alkanes will contaminate the multi-methyl-branched alkanes that are being withdrawn from the zone. To avoid contaminating the product effluent with the band of normal and mono-methyl-branched alkanes, the introduction of the desorbent is changed to the second adsorption zone so that the flow of desorbent is now reversed through the reaction zone and both adsorbent zones. The location where the product effluent is withdrawn is also moved to the first adsorbent zone in order to keep the effluent output downstream of the desorbent.

As discussed above, it is a requirement that the reaction zone contain a catalyst effective for isomerization. Such catalysts are well known in the art and suitable catalysts include, but are not limited to, platinum on mordenite, platinum and aluminum chloride on alumina, and platinum on sulfated or tungstated metal oxides such as zirconia. See generally, Kirk-Othmer *Encyclopedia of Chemical Technology,* 3rd ed,; Grayson, M., Eckroth, D., Eds., John Wiley & Sons: New York, Vol. 11 p 664, Vol. 12 pp 911 and 922, and Vol. 15 p 651. Depending upon the composition of the feed, several different catalysts may be combined in order to accomplish the catalysis function. The reaction zone may be one bed or several interconnected sub-beds.

When choosing a catalyst, the design of the reactor(s) and the operating temperature of the adsorbent that will be used must also be considered. If the reaction zone and the adsorbent zones are located within the same reaction vessel, both the adsorbent and the catalyst must be able to perform their respective functions at the same operating temperature. Such a configuration may be operated at typical hydrocarbon isomerization operating conditions including temperatures ranging from about 100° C. to about 300° C. and pressures from about 30 psig (206 kPag) to about 250 psig (1724 kPag). The operating conditions should be chosen so that all hydrocarbon components are in the same phase, gas or liquid. Since many of the suitable adsorbents perform better at lower temperatures, the preferred catalysts are platinum on tungstated zirconia or platinum on sulfated zirconia due to their high activity at lower temperatures. These catalysts are further preferred since operating at lower temperatures reduces the likelihood that the higher carbon atom compounds will undergo cracking. It is also possible that the reaction zone and each of the adsorption zones will be housed in separate vessels, thereby allowing for different operating parameters in each vessel. In that case, the operating parameters for each vessel may be independently established. Suitable operating conditions for the reaction zone and the adsorption zones include pressures in the range of from about 30 psig (206 kPag) to about 250 psig (1724 kPag) and temperatures in the range of from about 100° C. to about 300° C.

Each adsorption zone must contain an adsorbent. The same adsorbent or mixture of adsorbents may by employed in each of the adsorption zone, or each adsorption zone may contain a different adsorbent or mixture of adsorbents. The adsorbent is selected to have either a pore size capable of admitting normal or mono-methyl-branched alkane reactants but not the multi-methyl-branched isomerized products or to have selectivity for alkanes with no or low branching. In other words, the adsorbent must adsorb normal and mono-methyl-branched alkanes relative to muiti-methyl-branched alkanes. Any adsorbent meeting this criteria may be used in the process. Examples of suitable adsorbents include, but are not limited to, ferrierite, silicalite, zeolite X, zeolite Y, or zeolite Beta. Zeolite X, zeolite Y, or zeolite Beta may be ion exchanged with sodium, potassium, calcium, strontium, barium, or mixtures thereof. Similarly, the zeolites may be ion exchanged with transition metal ions, but this is less preferred due to the tendency for increased cracking with these ions. When the feed alkanes are a mixture of $C_6$ and $C_7$ alkanes, the most preferred adsorbent is silicalite. However, when the feed alkanes are either only $C_6$ alkanes or only $C_7$ alkanes, the most preferred adsorbent is a zeolite X ion exchanged with sodium.

The feed to the process must contain at least one normal or mono-methyl-branched alkane containing from about 6 to about 8 carbon atoms. The feed may be predominantly a single alkane or may be mixture of $C_6$ to $C_8$ alkanes. The feed may be largely normal alkanes, mono-methyl-branched alkanes, or a mixture thereof. Lighter hydrocarbons may be present, but will not produce the desired multi-methyl-branched alkanes. Examples of suitable alkanes include normal hexane, 2-methylpentane, 3-methylpentane, normal heptane, 2-methylhexane, 3-methylhexane, normal octane, 2-methylheptane, 3-methylheptane, and 4-methylheptane. Preferably the feed contains normal hexane, 2-methylpentane, 3-methylpentane, n-heptane, 2-methylheptane, 3-methylheptane, and 4-methylheptane. The feed is usually derived from other refinery processes and may contain some cyclic alkanes, olefinic hydrocarbons, aromatic hydrocarbons, and other hydrocarbons. The feed should not contain components that would significantly alter the capacities or selectivities of the desorbent or that would deactivate the catalyst.

For catalyst stability, hydrogen must be present in the reaction zone. The hydrogen may be introduced in a variety of ways, any of which would be appropriate provided sufficient hydrogen is present where needed to furnish the catalyst stabilizing function. The hydrogen to hydrocarbon mole ratio in the reaction zone should be within a range from about 0.1 to about 2. The hydrogen may be introduced with or independently of the feed or the desorbent, and it may be introduced continuously or in a pulsed manner. For convenience, it is preferred that the hydrogen be introduced with and in the same manner as the desorbent. Note that high quantities of hydrogen alone would provide a desorption function, but the desorption would be weak and inefficient. Incomplete desorption of normal alkanes would require that the adsorbent be periodically regenerated. Therefore, in the present invention, the quantity of hydrogen is limited only to that which is needed for catalyst stability. When the process of the present invention is operated in the liquid phase, the hydrogen may be dissolved in the liquid or may be controlled to be finely dispersed throughout the liquid. In this case, the liquid flowrate should be high enough to prevent accumulation of gas in the head space of the sub-beds.

The desorbent must contain at least one normal or mono-methyl-branched alkane containing from about 4 to about 8 carbons atoms and must be capable of desorbing the feed alkanes. Examples of acceptable alkanes for use in the desorbent include normal butane, 2-methylpropane, normal pentane, 2-methylbutane, normal hexane, 2-methylpentane, 3-methylpentane, normal heptane, 2-methyihexane, 3-methylhexane, normal octane, 2-methylheptane, 3-methylheptane, and 4-methylheptane. It is preferred that the desorbent alkane be capable of being isomerized since the branched alkanes which result from isomerization of the desorbent alkane are themselves octane boosters which may be blended into gasoline, thereby achieving an incremental octane number increase beyond that achieved through only isomerization of the alkanes present in the feed. For example, should normal pentane be used as a desorbent, 2-methylbutane would result as an incidental product. 2-Methylbutane is a valuable product in itself and may be blended with the gasoline pool to increase the octane number rating. Also, the mono-methyl-branched $C_5$ alkanes may be used as intermediates after dehydrogenation for such oxygenate products as methyl tertiarybutyl ether, ethyl tertiarybutyl ether, and tertiary amyl methyl ether. Therefore, the preferred desorbent alkane is a normal alkane and the most preferred is normal pentane.

The product stream withdrawn from an adsorption zone will contain the isomerized products of the feed, namely the multi-methyl-branched alkanes containing from about 6 to about 8 carbon atoms and desorbent. If the desorbent is isomerized, the product stream will contain a mixture of desorbent and isomerized products of the desorbent alkane.

The process of the present invention begins with the feed stream being introduced to the reaction zone. The feed stream may be introduced in any commonly known mode such as pulsed or continuous. The location of the feed introduction may be at any point within or close to the reaction zone. In a preferred embodiment, the feed stream is introduced at a location immediately upstream of the reaction zone at a position between the adsorbent zone receiving the desorbent input and the reaction zone. Initially, the desorbent is introduced to a first desorbent zone. When the fluid flow is reversed by redirecting the desorbent input to a second desorbent zone, the location of the feed input is also redirected so that the location of feed input remains at a position between the adsorbent zone receiving the desorbent input, now the second adsorbent zone, and the reaction zone. Each time the fluid flow is reversed, the location of the feed input is also changed so that the feed input remains between the adsorbent zone receiving desorbent input and the reaction zone.

Upon entering the reaction zone, the reactants in the feed contact the catalyst and undergo isomerization to form mono-methyl-branched and multi-methyl-branched alkanes. The fluid flow, directed by the flow of desorbent which is initially introduced to the first adsorption zone, carries the reaction mixture from the reaction zone into the second desorbent zone. Any normal or mono-methyl-branched alkanes present are adsorbed by the adsorbent and the multi-methyl-branched alkanes are relatively unadsorbed and thus are carried unhindered with the desorbent flow, and the product multi-methyl-branched alkanes are removed from the second adsorbent zone in a product stream as a mixture with desorbent. The normal or mono-methyl-branched alkanes are continuously being adsorbed by the adsorbent and eventually the capacity of the adsorbent will be approached or reached. If the capacity of the adsorbent is exceeded, breakthrough of the normal and mono-methyl-branched alkanes will occur and the product stream being removed will become contaminated with the normal and mono-methyl-branched alkanes. Therefore, as the maximum capacity of the adsorbent is approached, the fluid flow through the system is reversed by redirecting the input of the desorbent from the first adsorption zone to the second adsorption zone and concurrently redirecting the withdrawal of the product stream from the second adsorption zone to the first adsorption zone. The concentration of adsorbed normal and mono-methyl-branched alkanes is now adjacent to the desorbent input and will be desorbed and carried with the fluid flow from the second adsorption zone into the reaction zone. Upon contacting the catalyst in the reaction zone, the normal and mono-methyl-branched alkanes are isomerized to form additional product. Again, the reaction mixture is carried with the fluid flow from the reaction zone to the first adsorption zone. The normal and mono-methyl-branched alkanes are adsorbed and the product multi-methyl-branched alkanes are withdrawn from the first adsorption zone in a product stream. As the capacity of the adsorbent in the first adsorption zone is approached, the fluid flow is again reversed by redirecting the input of the desorbent from the second adsorption zone to the first adsorption zone and redirecting the withdrawal of the product stream from the first adsorption zone to the second adsorption zone. In this way, the normal and mono-methyl-branched alkanes continue to remain in the system and are able to contact the catalyst in the reaction zone and be isomerized to form additional multi-methyl-branched products thereby eliminating the need for recycle and reducing reactant waste. The process continues with the periodic reversal of fluid flow by alternating the input location of the desorbent from one adsorbent zone to another adsorbent zone and back.

The periodic reversals of fluid flow through the system are timed and the flowrates of the feed and desorbent are controlled so that the normal and mono-methyl-branched alkanes do not contaminate the product stream and remain within the system until they are isomerized to multi-methyl-branched alkanes. The reversals may also be timed to keep the residence time of the hydrocarbons in the reaction zone at a minimum, thereby reducing the degree of cracking. The alkane present in the desorbent may also undergo isomerization in the zone, but due to the volume of desorbent alkane present, it is expected that normal and isomerized desorbent alkanes will be present in the product stream. The product stream may be fractionated to recover at least a portion of the normal desorbent to be recycled to the process and further converted into isomerized desorbent.

What is claimed is:

1. A process for isomerization comprising:

a) introducing at least one normal or mono-methyl-branched alkane containing from about 6 to about 8 carbon atoms to a reaction zone to isomerize the normal or mono-methyl-branched alkane and form at least one multi-methyl-branched alkane, said reaction zone (I) operating under conditions effective for said isomerization, (II) containing a catalyst effective to catalyze said isomerization, (III) having a hydrogen atmosphere so that the mole ratio of hydrogen to hydrocarbon in the reaction zone is in the range of about 0.1 to about 2, and (IV) located between a first and a second adsorption zone;

b) introducing a desorbent consisting of an alkane having from about 4 to about 8 carbon atoms to the first adsorption zone and withdrawing an effluent containing at least one multi-methyl-branched alkane from the second adsorption zone thereby directing a fluid flow from the first adsorption zone through the reaction zone and to the second adsorption zone, said first and second adsorption zones containing an adsorbent effective to selectively adsorb normal and mono methyl-branched alkanes relative to multi-methyl-branched alkanes;

c) redirecting, after a period of time, the introduction of the desorbent to the second adsorption zone and concurrently moving the location of the withdrawal of the effluent to the first adsorption zone thereby redirecting the fluid flow from the second adsorption zone through the reaction zone and to the first adsorption zone; and d) continuing to alternate introducing the desorbent to the first adsorption zone and then the second adsorption zone while concurrently alternating withdrawing the effluent from the second adsorption zone and then the first adsorption zone thereby alternating the direction of the fluid flow through the adsorption zones and the reaction zone.

2. The process of claim 1 wherein all alkanes are in the gas phase.

3. The process of claim 1 wherein all alkanes are in the liquid phase.

4. The process of claim 1 wherein the desorbent is normal pentane.

5. The process of claim 1 wherein the catalyst is selected from the group consisting of platinum on mordenite, platinum and aluminum chloride on alumina, platinum on sulfated zirconia, and platinum on tungstated zirconia.

6. The process of claim 1 wherein the catalyst is platinum on tungstated zirconia.

7. The process of claim 1 wherein the catalyst is platinum on sulfated zirconia.

8. The process of claim 1 wherein the adsorbent is selected from the group consisting of zeolite X, zeolite Y, zeolite Beta, zeolite X ion exchanged with sodium, potassium, calcium, strontium, barium, and mixtures thereof, zeolite Y ion exchanged with sodium, potassium, calcium, strontium, barium, and mixtures thereof, zeolite Beta ion exchanged with sodium, potassium, calcium, strontium, barium, and mixtures thereof, silicalite, ferrierite and combinations thereof.

9. The process of claim 1 wherein the normal or mono-methyl-branched alkane is a mixture of alkanes containing 6 or 7 carbon atoms and the adsorbent is silicalite.

10. The process of claim 1 wherein the normal or mono-methyl-branched alkane is an alkane or mixture of alkanes containing 6 carbon atoms and the adsorbent is zeolite X ion exchanged with sodium.

11. The process of claim 1 wherein the normal or mono-methyl-branched alkane is an alkane or mixture of alkanes containing 7 carbon atoms and the adsorbent is zeolite X ion exchanged with sodium.

* * * * *